US010646624B2

(12) United States Patent
Hartwell (10) Patent No.: US 10,646,624 B2
(45) Date of Patent: *May 12, 2020

(54) APPARATUS AND METHOD FOR TOPICAL NEGATIVE PRESSURE THERAPY

(71) Applicant: Smith & Nephew PLC, Watford, Hertfordshire (GB)

(72) Inventor: Edward Hartwell, Hull (GB)

(73) Assignee: Smith & Nephew PLC, Watford (GB)

( * ) Notice: Subject to any disclaimer, the term of this patent is extended or adjusted under 35 U.S.C. 154(b) by 577 days.

This patent is subject to a terminal disclaimer.

(21) Appl. No.: 15/479,837

(22) Filed: Apr. 5, 2017

(65) Prior Publication Data

US 2017/0274124 A1    Sep. 28, 2017

Related U.S. Application Data

(63) Continuation of application No. 14/096,784, filed on Dec. 4, 2013, now Pat. No. 9,642,950, which is a
(Continued)

(30) Foreign Application Priority Data

Dec. 6, 2007 (GB) ................................ 07238769.9

(51) Int. Cl.
*A61M 1/00* (2006.01)
*A61M 31/00* (2006.01)
(Continued)

(52) U.S. Cl.
CPC ........ *A61M 1/0023* (2013.01); *A61M 1/0031* (2013.01); *A61M 1/0088* (2013.01);
(Continued)

(58) Field of Classification Search
CPC .............. A61M 1/0023; A61M 1/0031; A61M 1/0088; A61M 21/00; A61M 27/00; A61M 31/00; A61M 39/00; A61M 2205/3344
(Continued)

(56) References Cited

U.S. PATENT DOCUMENTS 3,276,472 A    10/1966    Jinkens et al.
3,750,704 A     8/1973    Burke et al.
(Continued)

FOREIGN PATENT DOCUMENTS

DE    20 2005 018 532    4/2006
GB         2307180       5/1997
(Continued)

OTHER PUBLICATIONS

Info V.A.C. User Manual—KCI—Dec. 2006, in 76 pages.
(Continued)

*Primary Examiner* — Andrew J Mensh
(74) *Attorney, Agent, or Firm* — Knobbe, Martens, Olson & Bear LLP (57) ABSTRACT

Apparatus and a method for the provision of topical negative pressure therapy to a wound site are described, the apparatus comprising: vacuum generating means for generating a negative pressure at said wound site said vacuum generating means being operably connected to a dressing at said wound site by aspiration conduit means; pressure sensing conduit means in fluid communication with said aspiration conduit means at a junction adjacent said dressing; first pressure sensing means between said junction and said vacuum generating means; second pressure sensing means operably associated with said pressure sensing conduit means; diagnostic means in communication with said first and second pressure sensing means; and control means in communica-
(Continued)

tion with said diagnostic means for controlling pressure in said aspiration and said pressure sensing conduit means.

29 Claims, 9 Drawing Sheets

Related U.S. Application Data continuation of application No. 12/746,499, filed as application No. PCT/GB2008/051048 on Nov. 11, 2008, now Pat. No. 8,617,129.

(51) Int. Cl.
*A61M 27/00* (2006.01)
*A61M 39/00* (2006.01)

(52) U.S. Cl.
CPC ............... *A61M 1/00* (2013.01); *A61M 27/00* (2013.01); *A61M 31/00* (2013.01); *A61M 39/00* (2013.01); *A61M 2205/3344* (2013.01)

(58) Field of Classification Search
USPC ........................................................ 604/319
See application file for complete search history.

(56) References Cited

U.S. PATENT DOCUMENTS

| | | | |
|---|---|---|---|
| 4,573,965 A * | 3/1986 | Russo | A61M 27/00 604/128 |
| 4,735,606 A * | 4/1988 | Davison | A61M 1/0084 604/118 |
| 4,936,834 A | 6/1990 | Beck et al. | |
| 5,207,641 A | 5/1993 | Allton | |
| 5,370,610 A | 12/1994 | Reynolds | |
| 5,514,088 A * | 5/1996 | Zakko | A61B 17/22 128/898 |
| 6,142,982 A | 11/2000 | Hunt et al. | |
| 6,979,324 B2 | 12/2005 | Bybordi et al. | |
| 7,302,950 B2 | 12/2007 | Berthon-Jones et al. | |
| 7,316,672 B1 | 1/2008 | Hunt et al. | |
| 7,553,306 B1 | 6/2009 | Hunt et al. | |
| 7,670,323 B2 | 3/2010 | Hunt et al. | |
| 7,758,555 B2 | 7/2010 | Kelch et al. | |
| 7,811,269 B2 | 10/2010 | Boynton et al. | |
| 8,012,169 B2 | 9/2011 | Joshi | |
| 8,267,918 B2 | 9/2012 | Johnson et al. | |
| 8,298,200 B2 | 10/2012 | Vess et al. | |
| 8,617,129 B2 | 12/2013 | Hartwell | |
| 8,784,392 B2 | 7/2014 | Vess et al. | |
| 8,843,327 B2 | 9/2014 | Vernon-Harcourt et al. | |
| 9,408,954 B2 | 8/2016 | Gordon et al. | |
| 9,642,950 B2 | 5/2017 | Hartwell | |
| 10,328,187 B2 | 6/2019 | Gordon et al. | |
| 2005/0131327 A1 | 6/2005 | Lockwood et al. | |
| 2005/0137539 A1 * | 6/2005 | Biggie | A61M 1/0088 604/313 |
| 2006/0258996 A1 | 11/2006 | Opie et al. | |
| 2008/0071216 A1 | 3/2008 | Locke et al. | |
| 2008/0300578 A1 | 12/2008 | Freedman | |
| 2009/0157016 A1 | 6/2009 | Adahan | |
| 2010/0160878 A1 | 6/2010 | Hunt et al. | |

FOREIGN PATENT DOCUMENTS

| | | |
|---|---|---|
| WO | WO 1992/12369 | 7/1992 |
| WO | WO 1999/19013 | 4/1999 |
| WO | WO 2004/016313 | 2/2004 |
| WO | WO 2004/037334 | 5/2004 |
| WO | WO 2005/046760 | 5/2005 |
| WO | WO 2005/046761 | 5/2005 |
| WO | WO 2005/046762 | 5/2005 |
| WO | WO 2005/061025 | 7/2005 |
| WO | WO 2005/105180 | 11/2005 |
| WO | WO 2007/031765 | 3/2007 |
| WO | WO 2007/087810 | 8/2007 |
| WO | WO 2007/106591 | 9/2007 |
| WO | WO 2008/141470 | 11/2008 |

OTHER PUBLICATIONS

International Preliminary Report on Patentability, re PCT Application No. PCT/GB2008/051048, dated Jun. 8, 2010.
International Search Report, re PCT Application No. PCT/GB2008/051048, dated Oct. 2, 2009.

\* cited by examiner

APPARATUS AND METHOD FOR TOPICAL NEGATIVE PRESSURE THERAPY

BACKGROUND

Technical Field

The present invention relates to apparatus and a method for the application of topical negative pressure (TNP) therapy to wounds. In particular, but not exclusively, the present invention relates to the control and monitoring of reduced pressure at a wound site.

Description of Related Art

There is much prior art available relating to the provision of apparatus and methods of use thereof for the application of TNP therapy to wounds together with other therapeutic processes intended to enhance the effects of the TNP therapy. Examples of such prior art include those listed and briefly described below.

TNP therapy assists in the closure and healing of wounds by reducing tissue oedema; encouraging blood flow and granulation of tissue; removing excess exudates and may reduce bacterial load and thus, infection to the wound. Furthermore, TNP therapy permits less outside disturbance of the wound and promotes more rapid healing.

In our co-pending International patent application, WO 2004/037334, apparatus, a wound dressing and a method for aspirating, irrigating and cleansing wounds are described. In very general terms, this invention describes the treatment of a wound by the application of topical negative pressure (TNP) therapy for aspirating the wound together with the further provision of additional fluid for irrigating and/or cleansing the wound, which fluid, comprising both wound exudates and irrigation fluid, is then drawn off by the aspiration means and circulated through means for separating the beneficial materials therein from deleterious materials. The materials which are beneficial to wound healing are recirculated through the wound dressing and those materials deleterious to wound healing are discarded to a waste collection bag or vessel.

In our co-pending International patent application, WO 2005/04670, apparatus, a wound dressing and a method for cleansing a wound using aspiration, irrigation and cleansing wounds are described. Again, in very general terms, the invention described in this document utilises similar apparatus to that in WO 2004/037334 with regard to the aspiration, irrigation and cleansing of the wound, however, it further includes the important additional step of providing heating means to control the temperature of that beneficial material being returned to the wound site/dressing so that it is at an optimum temperature, for example, to have the most efficacious therapeutic effect on the wound.

In our co-pending International patent application, WO 2005/105180, apparatus and a method for the aspiration, irrigation and/or cleansing of wounds are described. Again, in very general terms, this document describes similar apparatus to the two previously mentioned documents hereinabove but with the additional step of providing means for the supply and application of physiologically active agents to the wound site/dressing to promote wound healing.

The content of the above references is included herein by reference.

However, the above apparatus and methods are generally only applicable to a patient when hospitalised as the apparatus is complex, needing people having specialist knowledge in how to operate and maintain the apparatus, and also relatively heavy and bulky, not being adapted for easy mobility outside of a hospital environment by a patient, for example.

Some patients having relatively less severe wounds which do not require continuous hospitalisation, for example, but whom nevertheless would benefit from the prolonged application of TNP therapy, could be treated at home or at work subject to the availability of an easily portable and maintainable TNP therapy apparatus.

It is desirable to be able to differentiate between and to measure separately the pressures being applied immediately adjacent a vacuum pump connected to TNP apparatus and a dressing and the actual pressure being applied at or adjacent a wound dressing itself. This is because the pressure (reduction) being applied by a vacuum pump may not necessarily be that pressure which actually exists at the wound dressing. For example, an aspirant tube may be kinked or otherwise blocked, perhaps by aspirated fluids, and although a pressure measured by a sensor adjacent the pump may indicate that a desired pressure is being applied, the actual pressure at the wound site may be very different.

GB-A-2 307 180 describes a portable TNP therapy unit which may be carried by a patient clipped to belt or harness. The portable TNP apparatus described permits the measurement of pressure applied at the wound site and also that pressure generated by a vacuum pump. However, the means of conveying the respective pressures is by a multi-lumen tube which is complex and expensive to produce and which also requires a made-to-fit connector and dressing in order to connect the multi-lumen tube to a wound. Furthermore, the apparatus applies a vacuum to the dressing via the waste canister, therefore, the waste canister itself is a complex and expensive moulding needing to separate the various functions of the lumens in the multi-lumen tube and provide for the necessary routing thereof.

SUMMARY

It is an aim of the present invention to at least partly mitigate the above-mentioned problems in measuring pressures in known portable TNP apparatus.

It is an aim of embodiments of the present invention to provide portable TNP apparatus where pressures at different locations in the overall apparatus to dressing system may be easily and economically measured.

According to a first aspect of the present invention there is provided apparatus for the provision of topical negative pressure therapy to a wound site, the apparatus comprising: vacuum generating means for generating a negative pressure at said wound site said vacuum generating means being operably connected to a dressing at said wound site by aspiration conduit means; pressure sensing conduit means in fluid communication with said aspiration conduit means at a junction adjacent said dressing; first pressure sensing means between said junction and said vacuum generating means; second pressure sensing means operably associated with said pressure sensing conduit means; diagnostic means in communication with said first and second pressure sensing means; and control means in communication with said diagnostic means for controlling pressure in said aspiration and said pressure sensing conduit means.

The invention is comprised in part of an overall apparatus for the provision of TNP therapy to a patient in almost any environment. The apparatus is lightweight, may be mains or battery powered by a rechargeable battery pack contained within a device (henceforth, the term "device" is used to connote a unit which may contain all of the control, power supply, power supply recharging, electronic indicator means and means for initiating and sustaining aspiration functions to a wound and any further necessary functions of a similar nature). When outside the home, for example, the apparatus may provide for an extended period of operation on battery power and in the home, for example, the device may be connected to the mains by a charger unit whilst still being used and operated by the patient.

The overall apparatus of which the present invention is a part may comprise: a dressing covering the wound and sealing at least an open end of an aspiration conduit to a cavity formed over the wound by the dressing; an aspiration tube comprising at least one lumen therethrough leading from the wound dressing to a waste material canister for collecting and holding wound exudates/waste material prior to disposal; and, a power, control and aspiration initiating and sustaining device associated with the waste canister.

The dressing covering the wound may be any type of dressing normally employed with TNP therapy and, in very general terms, may comprise, for example, a semi-permeable, flexible, self-adhesive drape material, as is known in the dressings art, to cover the wound and seal with surrounding sound tissue to create a sealed cavity or void over the wound. There may aptly be a porous barrier and support member in the cavity between the wound bed and the covering material to enable an even vacuum distribution to be achieved over the area of the wound. The porous barrier and support member being, for example, a gauze, a foam, an inflatable bag or known wound contact type material resistant to crushing under the levels of vacuum created and which permits transfer of wound exudates across the wound area to the aspiration conduit sealed to the flexible cover drape over the wound.

The aspiration conduit means may be a plain flexible tube, for example, having a single lumen therethrough and made from a plastics material compatible with raw tissue, for example. A portion of the tube sited within the sealed cavity over the wound may have a structure to enable continued aspiration and evacuation of wound exudates without becoming constricted or blocked even at the higher levels of the negative pressure range envisaged. Where an aspiration conduit having a single lumen is combined into the dressing to aspirate the wound, the pressure sensing conduit may be connected in fluid communication with the aspiration conduit at a junction adjacent the dressing by means of a hollow "T" or "Y" piece, for example.

Alternatively to a plain single lumen conduit, the dressing over the wound site may be provided with a purpose made drain/aspirant conduit portion sealed to a dressing sealing film or drape and which is connected to the vacuum aspirant conduit and to the pressure sensing conduit means outside the dressing boundary. In this regard the drain/aspirant conduit portion may have a first portion resistant to being occluded or closed up due to the pressure applied thereto by the outer atmospheric pressure bearing down upon the drain portion via the sealing drape or film. The drain/aspirant conduit portion may also have an aspirant conduit portion having two lumens therethrough in the portion which exits the dressing. Such drain/aspirant conduit portions for incorporation into a dressing are available commercially and of low cost. One of the lumens may be connected to the aspiration conduit, vacuum generating means and first pressure sensing means and the second lumen to the pressure sensing conduit means and the second pressure sensing means. Thus the junction between the aspiration conduit means and the pressure sensing conduit means may be provided inside the dressing in the drain/aspirant conduit portion.

It is envisaged that the negative pressure range for the apparatus embodying the present invention may be between about −50 mmHg and −200 mmHg (note that these pressures are relative to normal ambient atmospheric pressure thus, −200 mmHg would be about 560 mmHg in practical terms). Aptly, the pressure range may be between about −75 mmHg and −150 mmHg. Alternatively a pressure range of up to −75 mmHg, up to −80 mmHg or over −80 mmHg can be used. Also aptly a pressure range of below −75 mmHg could be used. Alternatively a pressure range of over −100 mmHg could be used or over −150 mmHg.

The aspiration conduit at its distal end remote from the dressing may be attached to the waste canister at an inlet port or connector. The device containing the means for initiating and sustaining aspiration of the wound/dressing may be situated between the dressing and waste canister, however, in a preferred embodiment of the apparatus embodying the present invention, the device may aspirate the wound/dressing via the canister thus, the waste canister may preferably be sited between the wound/dressing and device.

The aspiration conduit at the waste material canister end may preferably be bonded to the waste canister to prevent inadvertent detachment when being caught on an obstruction, for example.

The canister may be a plastics material moulding or a composite unit comprising a plurality of separate mouldings. The canister may aptly be translucent or transparent in order to visually determine the extent of filling with exudates. However, the canister and device may in some embodiments provide automatic warning of imminent canister full condition and may also provide means for cessation of aspiration when the canister reaches the full condition.

The canister may be provided with filters to prevent the exhaust of liquids and odours therefrom and also to prevent the expulsion of bacteria into the atmosphere. Such filters may comprise a plurality of filters in series. Examples of suitable filters may comprise hydrophobic filters of 0.2 μm pore size, for example, in respect of sealing the canister against bacteria expulsion and 1 μm against liquid expulsion.

Aptly, the filters may be sited at an upper portion of the waste canister in normal use, that is when the apparatus is being used or carried by a patient the filters are in an upper position and separated from the exudate liquid in the waste canister by gravity. Furthermore, such an orientation keeps the waste canister outlet or exhaust exit port remote from the exudate surface.

Aptly the waste canister may be filled with an absorbent gel such as ISOLYSEL (trade mark), for example, as an added safeguard against leakage of the canister when full and being changed and disposed of. Added advantages of a gel matrix within the exudate storing volume of the waste canister are that it prevents excessive movement, such as slopping, of the liquid, minimises bacterial growth and minimises odours.

The waste canister may also be provided with suitable means to prevent leakage thereof both when detached from the device unit and also when the aspiration conduit is detached from the wound site/dressing.

The canister may have suitable means to prevent emptying by a user (without tools or damage to the canister) such that a full or otherwise end-of-life canister may only be disposed of with waste fluid still contained.

The device and waste canister may have mutually complementary means for connecting a device unit to a waste canister whereby the aspiration means in the device unit automatically connects to an evacuation port on the waste canister such that there is a continuous aspiration path from the wound site/dressing to an exhaust port on the device.

Aptly, the exhaust port from the fluid path through the apparatus is provided with filter means to prevent offensive odours from being ejected into the atmosphere.

In general terms the device unit comprises an aspirant pump; means for monitoring pressure applied by the aspirant pump, the first pressure sensing means; a flowmeter to monitor fluid flow through the aspirant pump; a control system which controls the aspirant pump in response to signals from sensors such as the pressure monitoring means and the flowmeter, for example, and which control system also controls a power management system with regard to an on-board battery pack and the charging thereof and lastly a user interface system whereby various functions of the device such as pressure level set point, for example, may be adjusted (including stopping and starting of the apparatus) by a user. The device unit may contain all of the above features within a single unified casing.

In the present invention the device may also include the second pressure sensor connected to the pressure sensing conduit means and the diagnostic means. The diagnostic means may be comprised in the control system to receive signals from the first and second pressure sensors and, in response to software in the control, system operate various functions depending upon the signals received.

The pressure sensing conduit may be connected to a valve which when closed effectively forms with pressure sensing conduit a closed branch of the aspiration conduit and in which branch the second pressure sensing means is located. Depending upon the signals received by the control system from the first and second pressure sensing means, the control system may open the valve effectively to expose the pressure sensing conduit to atmospheric pressure. The response in pressures sensed by the first and second pressure sensor means may be related to software in the control system and trigger appropriate alarms depending on the pressure responses. For example, the control system may be provided with software which recognises when the difference in pressure between the aspirant conduit and the pressure sensing conduit as sensed by the first and second pressure sensing means reaches or exceeds a predetermined level. When this happens the control system may open the valve to atmosphere. If, for example, there is a kink in the aspiration conduit effectively stopping flow in the aspirant conduit then the first pressure sensing means will continue to read a pressure equal to a preset pressure for the vacuum pump to achieve whereas the second pressure sensing means will show atmospheric pressure. The control system may issue an appropriate alarm to check the condition of the aspirant conduit means. Alternatively, if the aspirant conduit means is not blocked due to a kink, for example, it may be blocked due to the waste canister being full and unable to accept any more wound exudate fluid, in which case the control system will issue an alarm to the need to replace the waste canister and/or check the aspirant conduit. In the event that the aspirant conduit is blocked merely due to aspirated wound exudate then opening of the valve will admit air into the system and enable the vacuum pump to aspirate the exudate into the waste canister and so clear the aspirant conduit. In this latter case on opening the valve the pressure sensed by the first pressure sensor mean swill initially be that of the vacuum level set by the user or clinician and that sensed by the second pressure sensor will be atmospheric. However, after a short time the vacuum pump will clear the aspirant conduit and the pressure sensed by both pressure sensor means will be substantially atmospheric or close thereto at which point the control system, in response to information stored in the memory thereof will close the valve and normal operation of the apparatus will be resumed. Where there is a leak of ambient air into the system due, for example, to an inadequately applied dressing drape, then the pressures sensed by the two sensor means will be approximately equal and in which case the control system will not open the valve but information in the control system memory related, for example, to the rate of pumping of the vacuum pump and the rate of attaining a required vacuum level being lower than specified may trigger an alarm that the dressing integrity may need checking, for example.

The valve may preferably be provided with a microbial filter to ensure that bacteria cannot either enter the device or be expelled to atmosphere.

In view of the fact that the device unit contains the majority of the intrinsic equipment cost therein ideally it will also be able to survive impact, tolerate cleaning in order to be reusable by other patients.

In terms of pressure capability the aspiration means may be able to apply a maximum pressure drop of at least −200 mmHg to a wound site/dressing. The apparatus is capable of maintaining a predetermined negative pressure even under conditions where there is a small leak of air into the system and a high exudate flow.

The pressure control system may prevent the minimum pressure achieved from exceeding for example −200 mmHg so as not to cause undue patient discomfort. The pressure required may be set by the user at a number of discreet levels such as −50, −75, −100, −125, −150, −175 mmHg, for example, depending upon the needs of the wound in question and the advice of a clinician. Thus suitable pressure ranges in use may be from −25 to −80 mmHg, or −50 to −76 mmHg, or −50 to −75 mmHg as examples. The control system may also advantageously be able to maintain the set pressure within a tolerance band of +/−10 mmHg of the set point for 95% of the time the apparatus is operating given that leakage and exudation rates are within expected or normal levels.

Aptly, the control system may trigger alarm means such as a flashing light, buzzer or any other suitable means when various abnormal conditions apply such as, for example: pressure outside set value by a large amount due to a gross leak of air into system; duty on the aspiration pump too high due to a relatively smaller leakage of air into the system; pressure differential between wound site and pump is too high due, for example, to a blockage or waste canister full.

The apparatus of the present invention may be provided with a carry case and suitable support means such as a shoulder strap or harness, for example. The carry case may be adapted to conform to the shape of the apparatus comprised in the joined together device and waste canister. In particular, the carry case may be provided with a bottom opening flap to permit the waste canister to be changed without complete removal of the apparatus form the carry case.

The carry case may be provided with an aperture covered by a displaceable flap to enable user access to a keypad for varying the therapy applied by the apparatus.

According to a second aspect of the present invention, there is provided a method for the topical negative pressure treatment of a wound site using the apparatus of the first aspect, the method comprising the steps of: providing vacuum generating means for generating a negative pressure at said wound site said vacuum generating means being operably connected to a dressing at said wound site by aspiration conduit means; providing pressure sensing conduit means in fluid communication with said aspiration conduit means at a junction adjacent said dressing; providing first pressure sensing means between said junction and said vacuum generating means; providing second pressure sensing means operably associated with said pressure sensing conduit means; providing diagnostic means in communication with said first and second pressure sensing means; and providing control means in communication with said diagnostic means for controlling pressure in said aspiration and said pressure sensing conduit means; sensing pressures at said first and second pressure sensor means and triggering an appropriate alarm when pressure levels sensed by said sensor means lie outside of a preset pressure differential stored in memory means in said control system.

Desirably, said method also includes the optional provision of valve means associated with the pressure sensing conduit means, said valve being controlled by said control system to open and close said pressure sensing conduit means to atmospheric pressure.

According to a third aspect of the present invention there is provided a drainage conduit member for use in topical negative pressure therapy, the drainage conduit member comprising an exudate collecting portion having a plurality of exudate aspiration flow apertures therein, the exudate collecting portion being contained, in use, beneath a wound covering and sealing dressing drape; an aspirant conduit portion having a single lumen therethrough in fluid communication with the exudate collecting portion; and a dual lumen portion having both lumens in fluid communication with the single lumen aspirant conduit portion.

The exudate collecting portion may comprise a flattened shape having two opposing walls each having exudate flow apertures therein for collecting wound exudate, the two opposing walls may be joined by side pieces thereby forming a chamber in the flattened portion which chamber being in fluid flow communication with one end of the single lumen aspirant conduit portion. The opposing wall portions may be provided with internal ribs within the chamber formed, to prevent the inner surfaces of the two opposing walls from contacting each other and so closing the chamber within to exudate fluid flow. The ribs holding the walls apart under vacuum conditions to permit continuous fluid flow therethrough.

The dual lumen portion may provide one portion for aspirated exudate fluid flow therethrough towards a waste canister whilst the second lumen may, for example, be provided for the purpose of admitting an air bleed into the system, preferably close to the dressing, so as to ensure continuous aspirant fluid flow under all conditions.

The flattened shaped exudate collecting portion may be formed in other shapes and constructions according to the requirements of a particular wound formation.

According to a fourth aspect of the present invention there is provided an adapter for use in topical negative pressure therapy, the adapter comprising a connecting spigot portion having a fluid flow inlet conduit therethrough; a body portion wherein the inlet conduit communicates with two fluid flow passages; the body portion also including means for receiving two fluid flow lumens, both fluid flow lumens being in fluid communication with each other in the body portion.

The adapter may be used to connect to a single lumen aspirant conduit exiting a sealed wound cavity under a dressing drape during TNP therapy; one lumen in the adapter being for aspiration of wound exudate to an associated waste canister and the second lumen being for admitting an air bleed into the system, preferably close to the dressing so as to ensure continuous aspiration of fluid from the wound cavity.

BRIEF DESCRIPTION OF THE DRAWINGS

In order that the present invention may be more fully understood, examples will now be described by way of illustration only with reference to the accompanying drawings, of which.

DETAILED DESCRIPTION

Referring now to FIGS. 1 to 4 of the drawings and where the same or similar features are denoted by common reference numerals.

Figure 1:
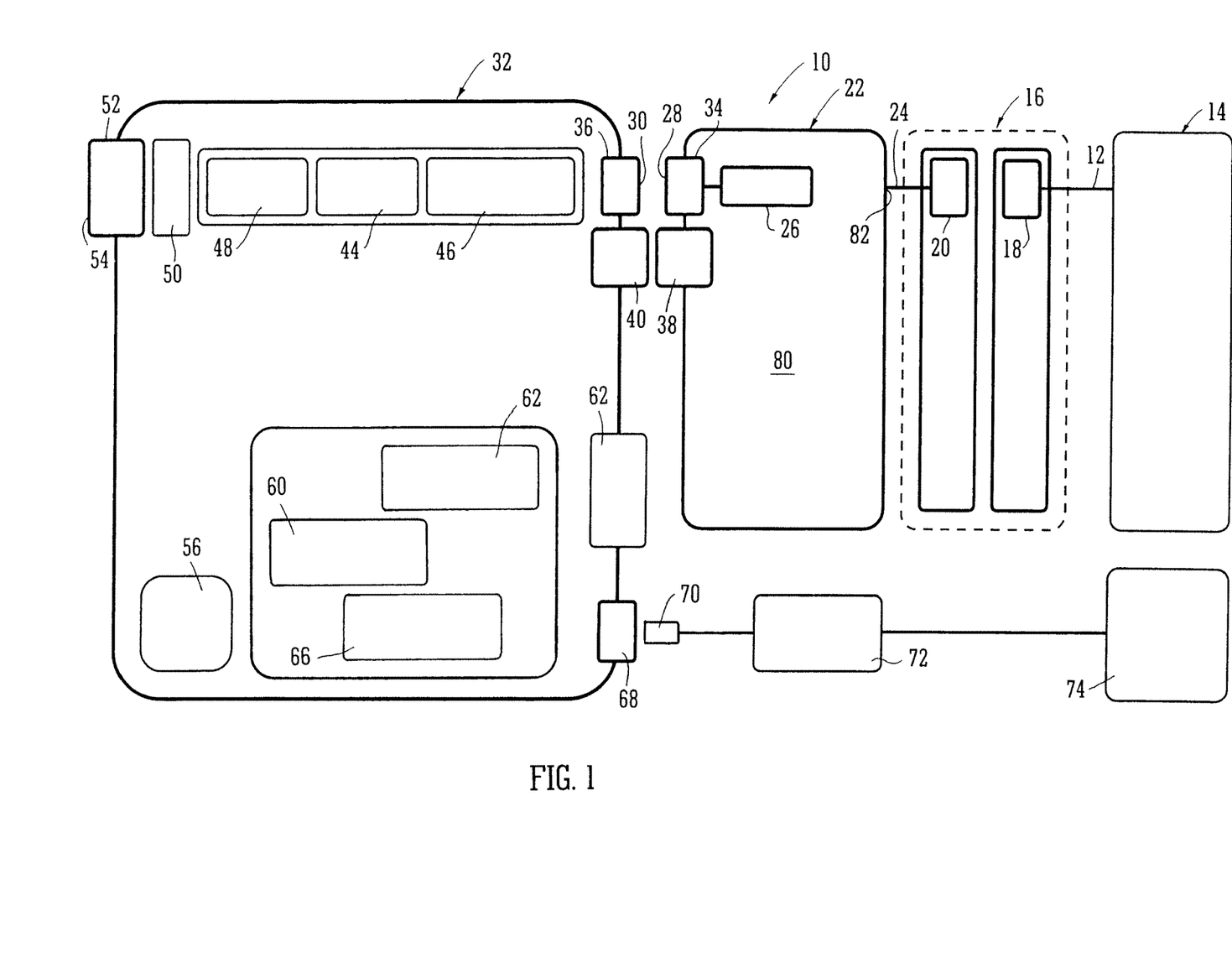
FIG. 1 shows a generalised schematic block diagram showing a general view of an apparatus and the constituent apparatus features thereof.

FIG. 1 shows a generalised schematic view of an apparatus 10 of a portable topical negative pressure (TNP) system. It will be understood that embodiments of the present invention are generally applicable to use in such a TNP system. Briefly, negative pressure wound therapy assists in the closure and healing of many forms of "hard to heal" wounds by reducing tissue oedema; encouraging blood flow and granular tissue formation; removing excess exudate and may reduce bacterial load (and, therefore, infection). In addition the therapy allows for less disturbance of a wound leading to more rapid healing. The TNP system is detailed further hereinafter but in summary includes a portable body including a canister and a device with the device capable of providing an extended period of continuous therapy within at least a one year life span. The system is connected to a patient via a length of tubing with an end of the tubing operably secured to a wound dressing on the patient.

More particularly, as shown in FIG. 1, the apparatus comprises an aspiration conduit 12 operably and an outer surface thereof at one end sealingly attached to a dressing 14. The dressing 14 will not be further described here other than to say that it is formed in a known manner from well know materials to those skilled in the dressings art to create a sealed cavity over and around a wound to be treated by TNP therapy with the apparatus of the present invention. The aspiration conduit has an in-line connector 16 comprising connector portions 18, 20 intermediate its length between the dressing 14 and a waste canister 22. The aspiration conduit between the connector portion 20 and the canister 22 is denoted by a different reference numeral 24 although the fluid path through conduit portions 12 and 24 to the waste canister is continuous. The connector portions 18, 20 join conduit portions 12, 24 in a leak-free but disconnectable manner. The waste canister 22 is provided with filters 26 which prevent the escape via an exit port 28 of liquid and bacteria from the waste canister. The filters may comprise a 1 μm hydrophobic liquid filter and a 0.2 μm bacteria filter such that all liquid and bacteria is confined to an interior waste collecting volume of the waste canister 22. The exit port 28 of the waste canister 22 mates with an entry/suction port 30 of a device unit 32 by means of mutually sealing connector portions 34, 36 which engage and seal together automatically when the waste canister 22 is attached to the device unit 32, the waste canister 22 and device unit 32 being held together by catch assemblies 38, 40. The device unit 32 comprises an aspirant pump 44, an aspirant pressure monitor 46 and an aspirant flowmeter 48 operably connected together. The aspiration path takes the aspirated fluid which in the case of fluid on the exit side of exit port 28 is gaseous through a silencer system 50 and a final filter 52 having an activated charcoal matrix which ensures that no odours escape with the gas exhausted from the device 32 via an exhaust port 54. The filter 52 material also serves as noise reducing material to enhance the effect of the silencer system 50. The device 32 also contains a battery pack 56 to power the apparatus which battery pack also powers the control system 60 which controls a user interface system 62 controlled via a keypad (not shown) and the aspiration pump 44 via signals from sensors 46, 48. A power management system 66 is also provided which controls power from the battery pack 56, the recharging thereof and the power requirements of the aspirant pump 44 and other electrically operated components. An electrical connector 68 is provided to receive a power input jack 70 from a SELV power supply 72 connected to a mains supply 74 when the user of the apparatus or the apparatus itself is adjacent a convenient mains power socket.

Figure 2:
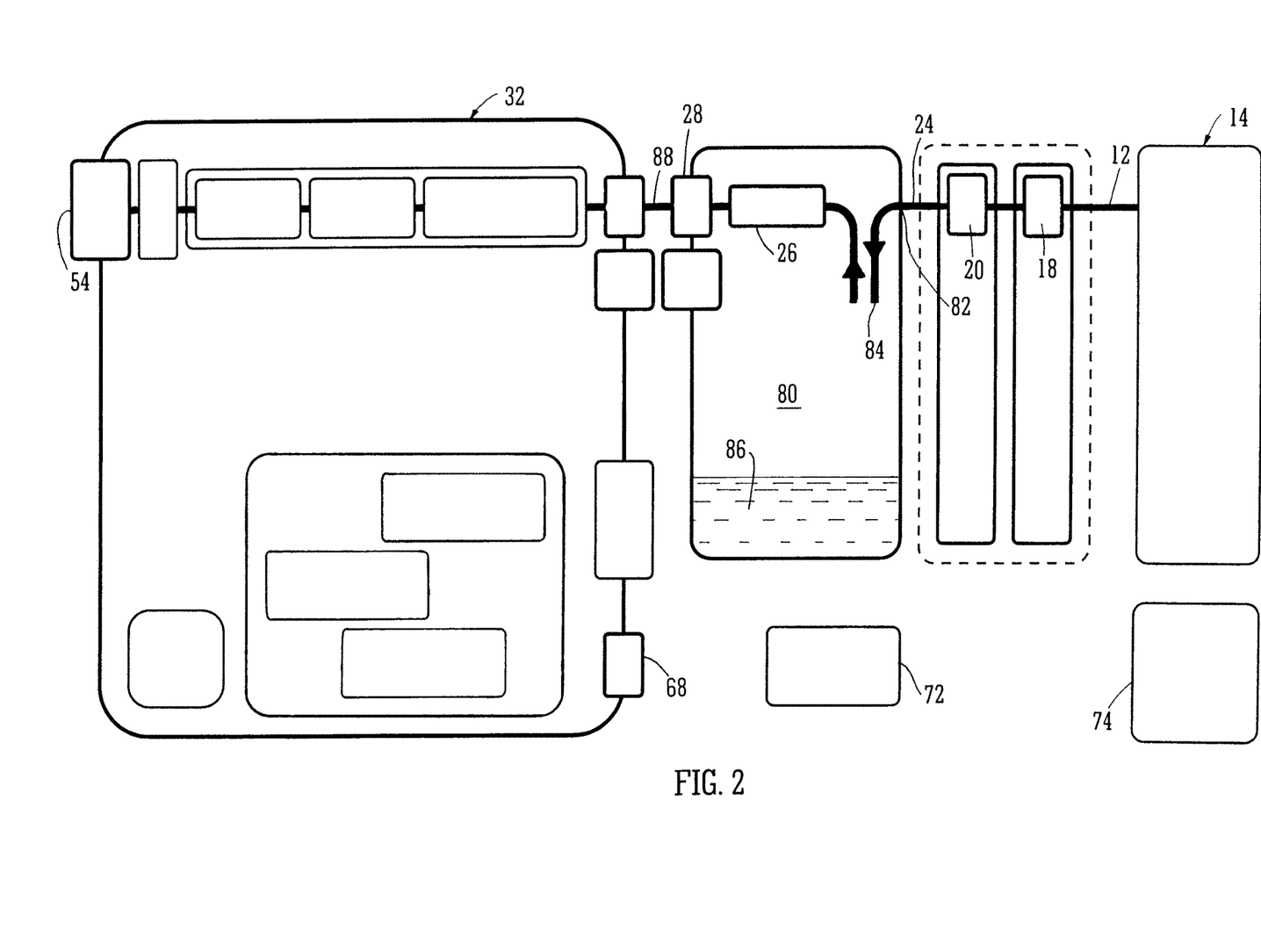
FIG. 2 shows a similar generalised schematic block diagram to FIG. 1 and showing fluid paths therein.

FIG. 2 shows a similar schematic representation to FIG. 1 but shows the fluid paths in more detail. The wound exudate is aspirated from the wound site/dressing 14 via the conduit 12, the two connector portions 18, 20 and the conduit 24 into the waste canister 22. The waste canister 22 comprises a relatively large volume 80 in the region of 500 ml into which exudate from the wound is drawn by the aspiration system at an entry port 82. The fluid 84 drawn into the canister volume 80 is a mixture of both air drawn into the dressing 14 via the semi-permeable adhesive sealing drape (not shown) and liquid 86 in the form of wound exudates. The volume 80 within the canister is also at a lowered pressure and the gaseous element 88 of the aspirated fluids is exhausted from the canister volume 80 via the filters 26 and the waste canister exhaust exit port 28 as bacteria-free gas. From the exit port 28 of the waste canister to the final exhaust port 54 the fluid is gaseous only.

Figure 3:
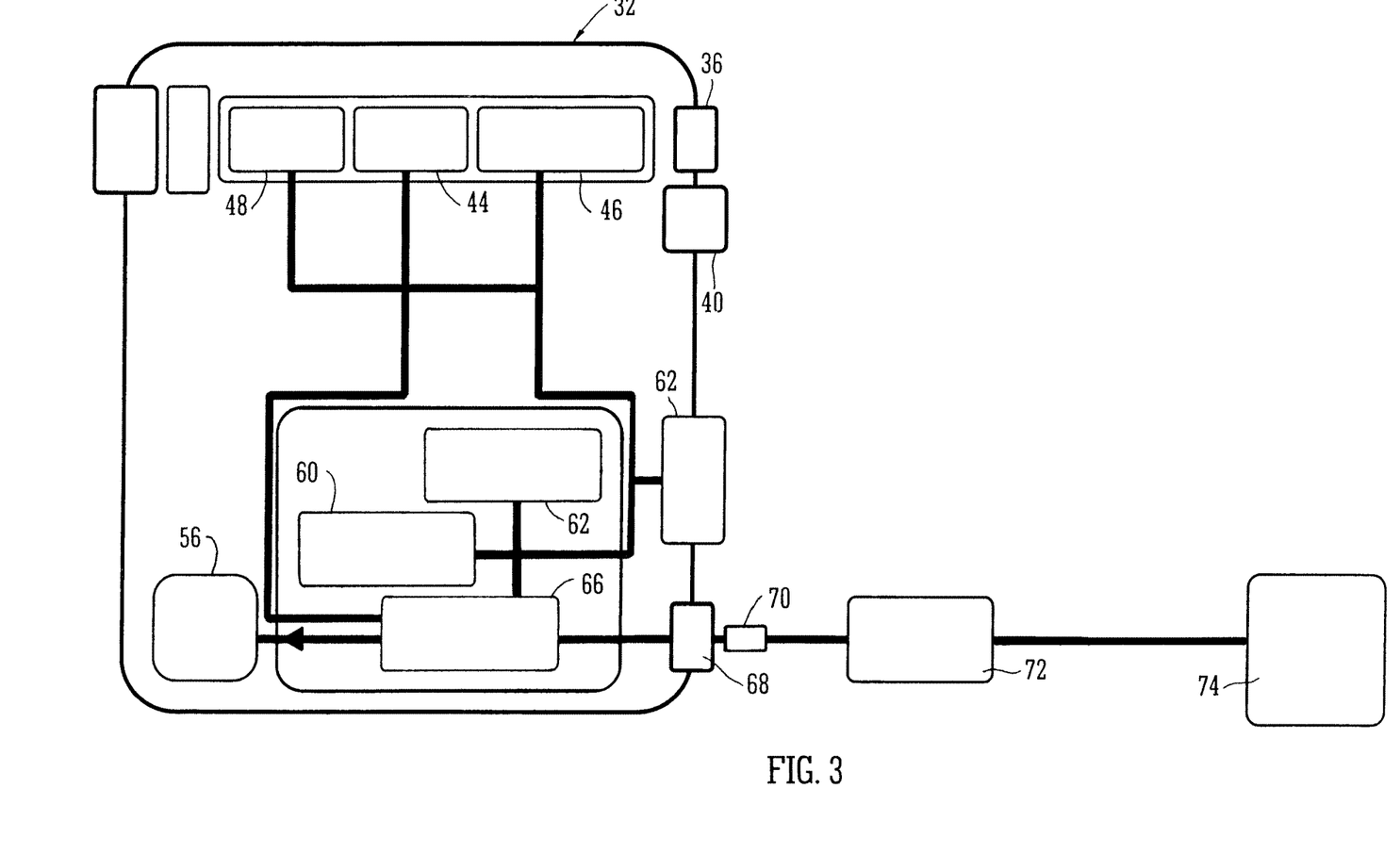
FIG. 3 shows a generalised schematic block diagram similar to FIG. 1 but of a device unit only and showing power paths for the various power consuming/producing features of the apparatus.

FIG. 3 shows a schematic diagram showing only the device portion of the apparatus and the power paths in the device of the apparatus embodying the present invention. Power is provided mainly by the battery pack 56 when the user is outside their home or workplace, for example, however, power may also be provided by an external mains 74 supplied charging unit 72 which when connected to the device 32 by the socket 68 is capable of both operating the device and recharging the battery pack 56 simultaneously. The power management system 66 is included so as to be able to control power of the TNP system. The TNP system is a rechargeable, battery powered system but is capable of being run directly from mains electricity as will be described hereinafter more fully with respect to the further figures. If disconnected from the mains the battery has enough stored charge for approximately 8 hours of use in normal conditions. It will be appreciated that batteries having other associated life times between recharge can be utilised. For example batteries providing less than 8 hours or greater than 8 hours can be used. When connected to the mains the device will run off the mains power and will simultaneously recharge the battery if depleted from portable use. The exact rate of battery recharge will depend on the load on the TNP system. For example, if the wound is very large or there is a significant leak, battery recharge will take longer than if the wound is small and well sealed.

Figure 4:
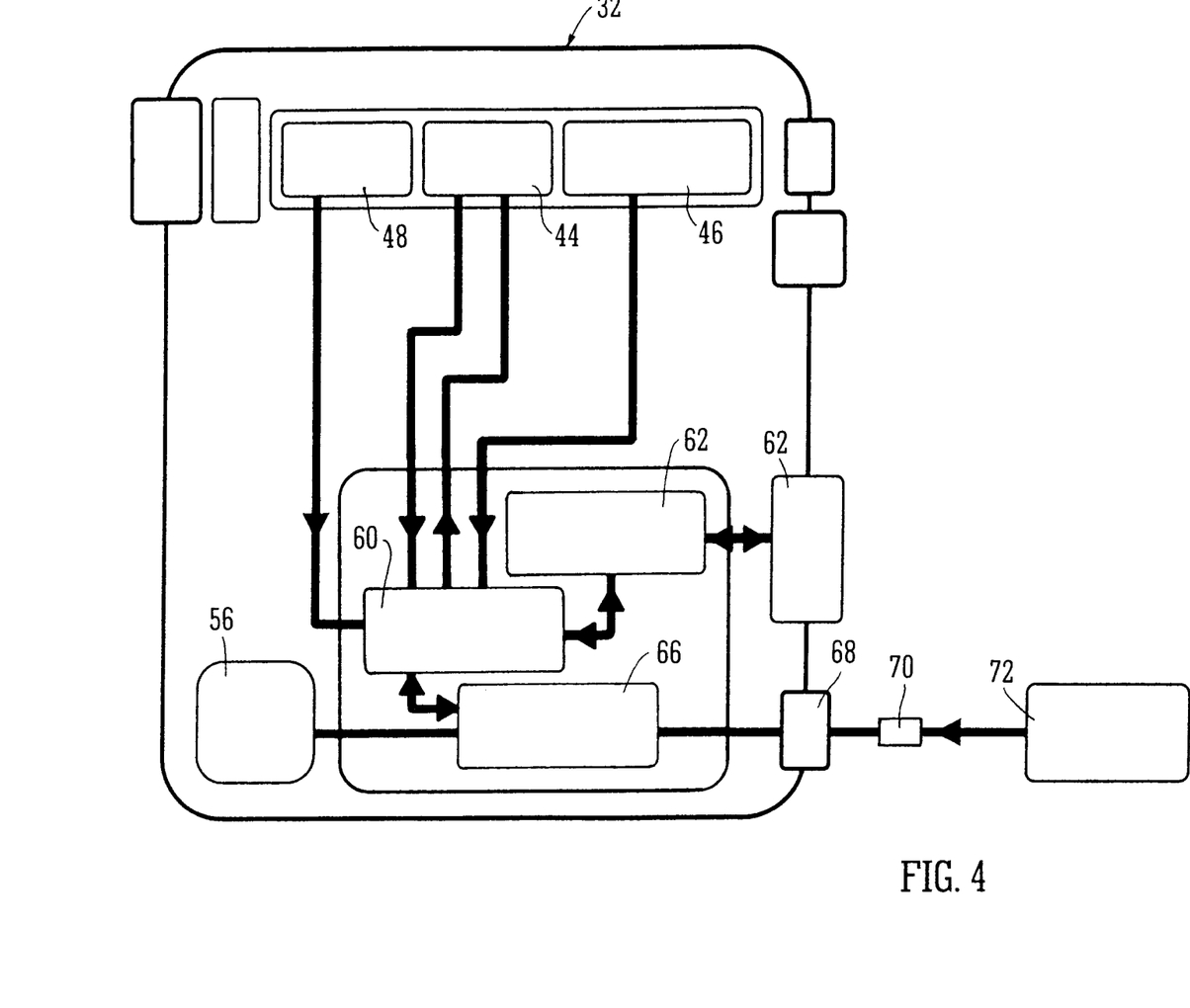
FIG. 4 shows a similar generalised schematic block diagram to FIG. 3 of the device unit and showing control system data paths for controlling the various functions and components of the apparatus.
Figure 5:
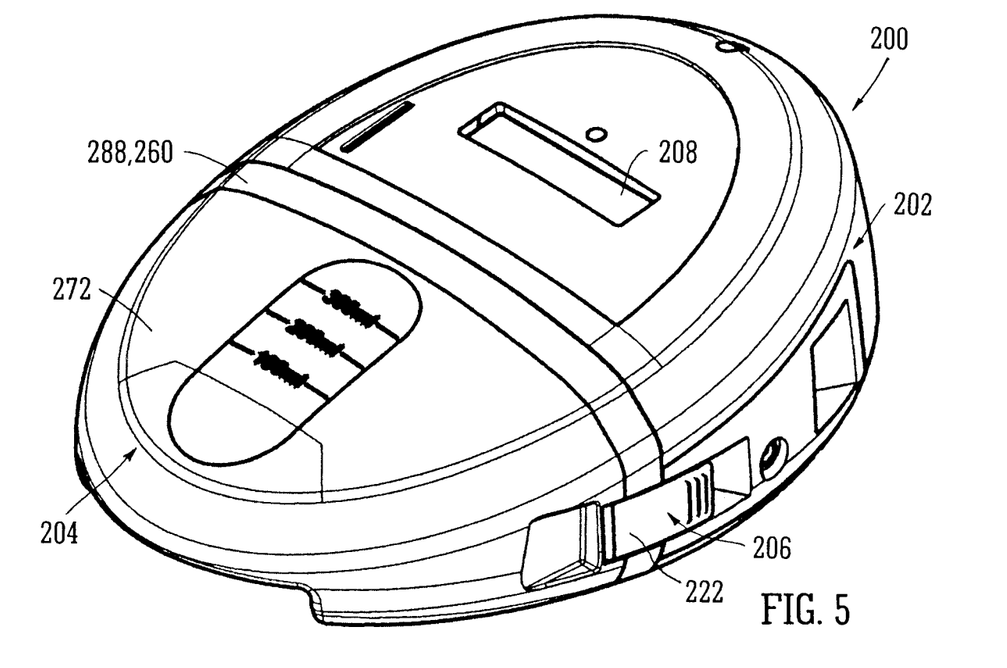
FIG. 5 shows a perspective view of an apparatus.
Figure 6:
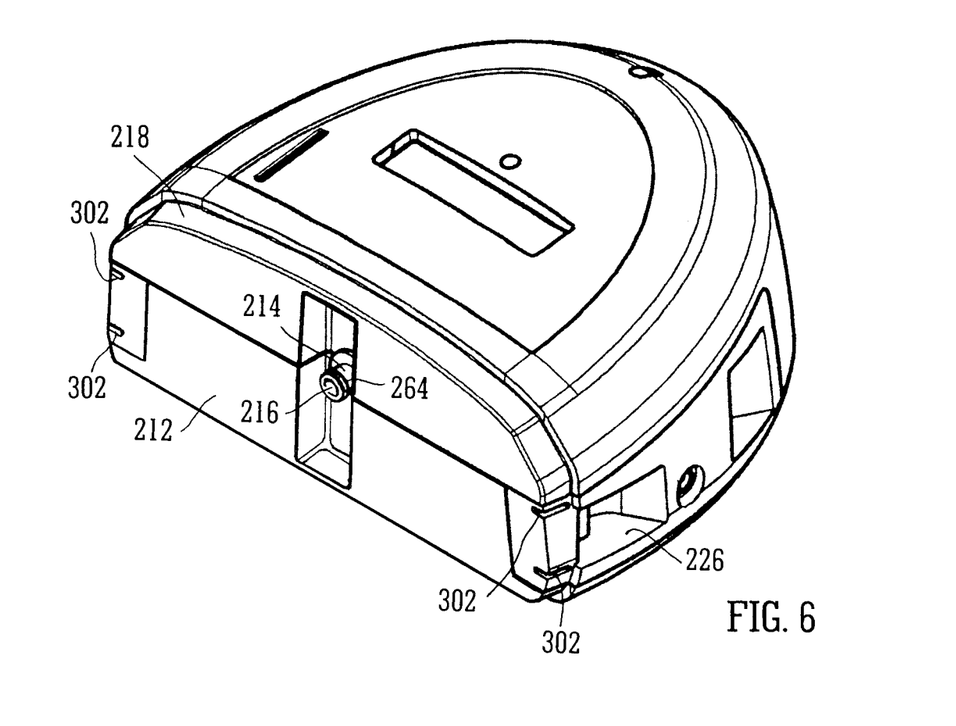
FIG. 6 shows a perspective view of an assembled device unit of the apparatus of FIG. 5.
Figure 7:
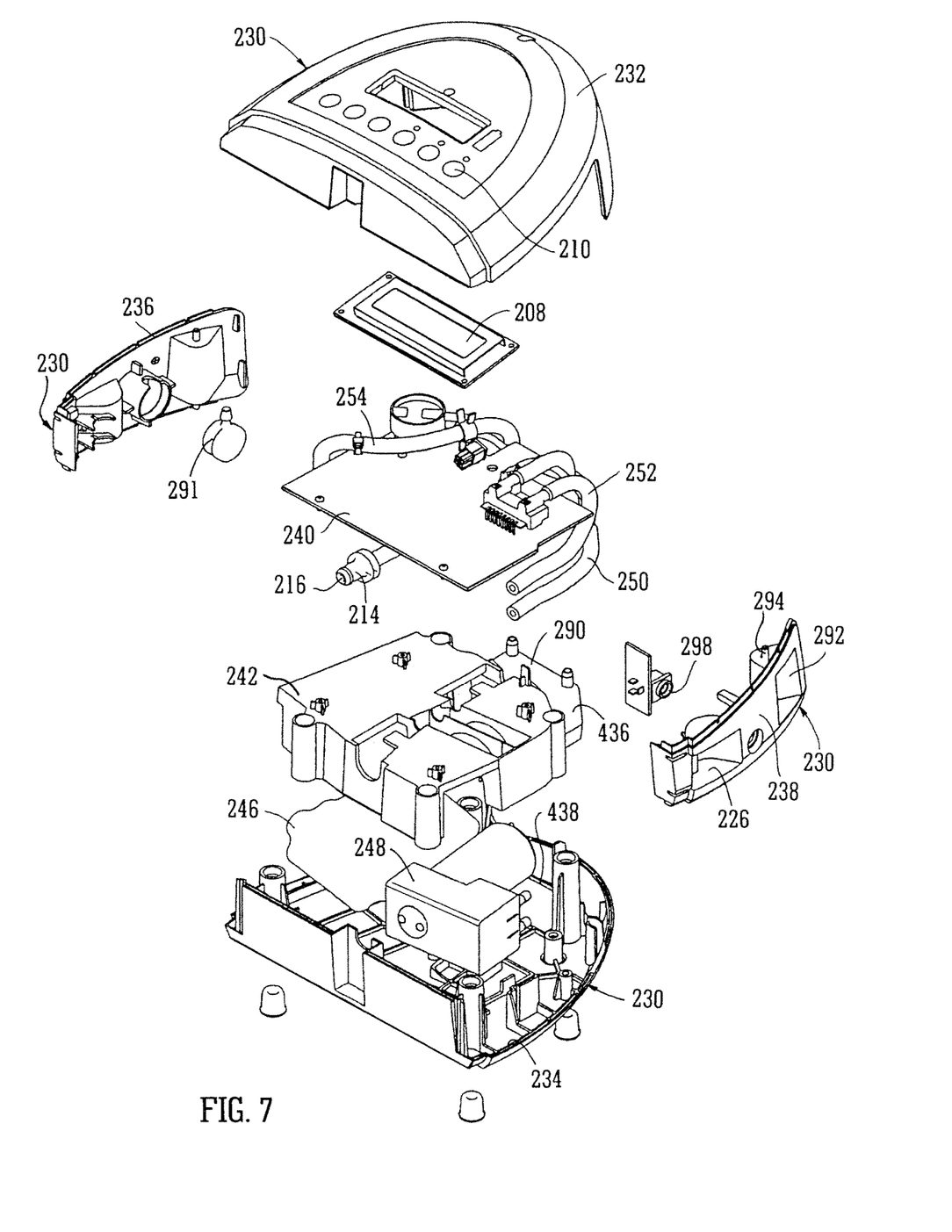
FIG. 7 shows an exploded view of the device unit of FIG. 6.

FIG. 4 shows the device 32 part of the apparatus embodying the present invention and the data paths employed in the control system for control of the aspirant pump and other features of the apparatus. A key purpose of the TNP system is to apply negative pressure wound therapy. This is accomplished via the pressure control system which includes the pump and a pump control system. The pump applies negative pressure; the pressure control system gives feedback on the pressure at the pump head to the control system; the pump control varies the pump speed based on the difference between the target pressure and the actual pressure at the pump head. In order to improve accuracy of pump speed and hence provide smoother and more accurate application of the negative pressure at a wound site, the pump is controlled by an auxiliary control system. The pump is from time to time allowed to "free-wheel" during its duty cycle by turning off the voltage applied to it. The spinning motor causes a "back electro-motive force" or BEMF to be generated. This BEMF can be monitored and can be used to provide an accurate measure of pump speed. The speed can thus be adjusted more accurately than can prior art pump systems.

In some embodiments of apparatus, actual pressure at a wound site may not be measured but the difference between a measured pressure (at the pump) and the wound pressure is minimised by the use of large filters and large bore tubes wherever practical. If the pressure control measures that the pressure at the pump head is greater than a target pressure (closer to atmospheric pressure) for a period of time, the device sends an alarm and displays a message alerting the user to a potential problem such as a leak.

In addition to pressure control a separate flow control system can be provided. A flow meter may be positioned after the pump and is used to detect when a canister is full or the tube has become blocked. If the flow falls below a certain threshold, the device sounds an alarm and displays a message alerting a user to the potential blockage or full canister.

Figure 8:
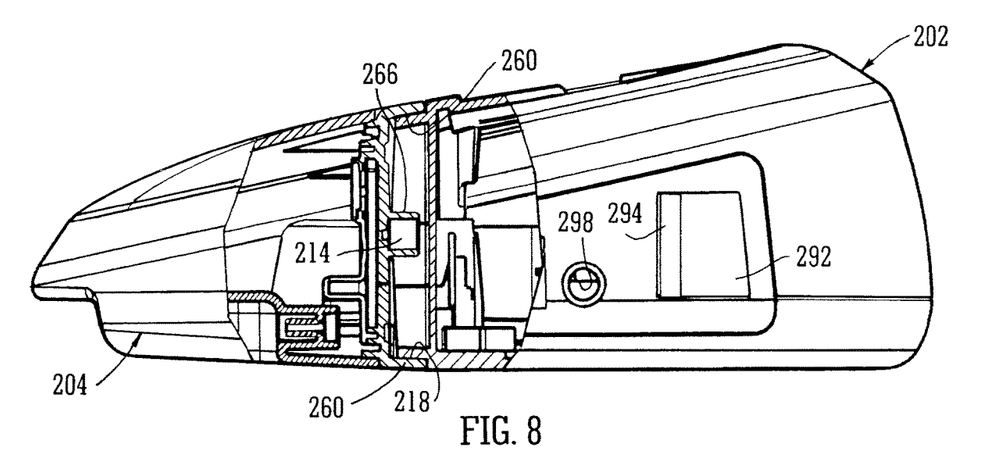
FIG. 8 shows a partially sectioned side elevation view through the interface between a waste canister and device unit of the apparatus.
Figure 9:
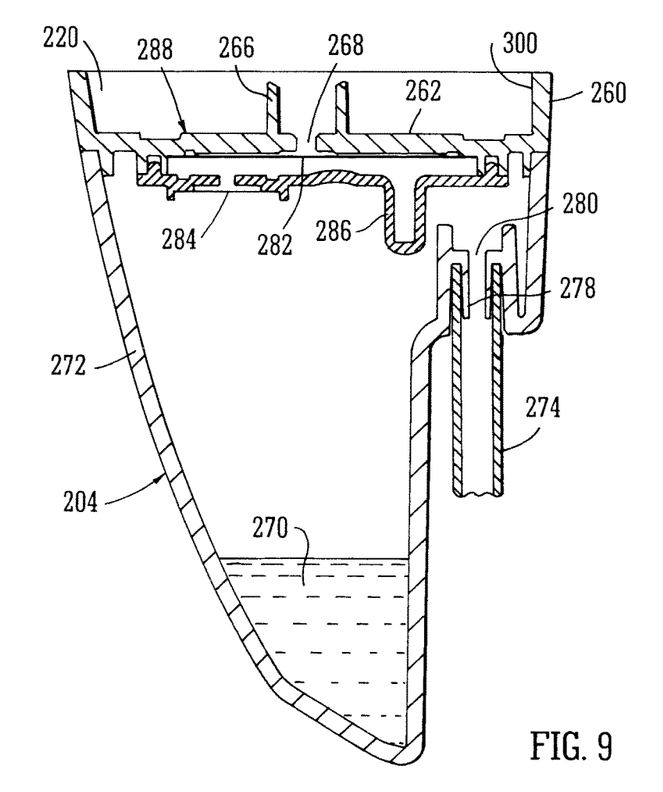
FIG. 9 shows a cross section through a waste canister of the apparatus of FIGS. 5 to 8.

Referring now to FIGS. 5 to 9 which show various views and cross sections of a preferred embodiment of apparatus 200 embodying the present invention. The preferred embodiment is of generally oval shape in plan and comprises a device unit 202 and a waste canister 204 connected together by catch arrangements 206. The device unit 202 has a liquid crystal display (LCD) 208, which gives text based feedback on the wound therapy being applied, and a membrane keypad 210, the LCD being visible through the membrane of the keypad to enable a user to adjust or set the therapy to be applied to the wound (not shown). The device has a lower, generally transverse face 212 in the centre of which is a spigot 214 which forms the suction/entry port 216 to which the aspiration means (to be described below) are connected within the device unit. The lower edge of the device unit is provided with a rebated peripheral male mating face 218 which engages with a co-operating peripheral female formation 220 on an upper edge of the waste canister 204 (see FIGS. 8 and 9). On each side of the device 202, clips 222 hinged to the canister 204 have an engaging finger (not shown) which co-operates with formations in recesses 226 in the body of the device unit. From FIG. 7 it may be seen that the casing 230 of the device unit is of largely "clamshell" construction comprising front and back mouldings 232, 234, respectively and left-hand and right-hand side inserts 236, 238. Inside the casing 230 is a central chassis 240 which is fastened to an internal moulded structural member 242 and which chassis acts as a mounting for the electrical circuitry and components and also retains the battery pack 246 and aspiration pump unit 248. Various tubing items 250, 252, 254 connect the pump unit 248 and suction/entry port 216 to a final gaseous exhaust via a filter 290. FIG. 8 shows a partially sectioned side elevation of the apparatus 200, the partial section being around the junction between the device unit 202 and the waste canister 204, a cross section of which is shown at FIG. 9. Theses views show the rebated edge 218 of the male formation on the device unit co-operating with the female portion 220 defined by an upstanding flange 260 around the top face 262 of the waste canister 204. When the waste canister is joined to the device unit, the spigot 214 which has an "0" ring seal 264 therearound sealingly engages with a cylindrical tube portion 266 formed around an exhaust/exit port 268 in the waste canister. The spigot 214 of the device is not rigidly fixed to the device casing but is allowed to "float" or move in its location features in the casing to permit the spigot 214 and seal 264 to move to form the best seal with the bore of the cylindrical tube portion 266 on connection of the waste canister to the device unit. The waste canister 204 in FIG. 9 is shown in an upright orientation much as it would be when worn by a user. Thus, any exudate 270 would be in the bottom of the internal volume of waste receptacle portion 272. An aspiration conduit 274 is permanently affixed to an entry port spigot 278 defining an entry port 280 to receive fluid aspirated from a wound (not shown) via the conduit 274. Filter members 282 comprising a 0.2 μm filter and 284 comprising a 1 μm filter are located by a filter retainer moulding 286 adjacent a top closure member or bulkhead 288 the filter members preventing any liquid or bacteria from being drawn out of the exhaust exit port 268 into the pump and aspiration path through to an exhaust and filter unit 290 which is connected to a casing outlet moulding at 291 via an exhaust tube (not shown) in casing side piece 236. The side pieces 236, 238 are provided with recesses 292 having support pins 294 therein to locate a carrying strap (not shown) for use by the patient. The side pieces 230 and canister 204 are also provided with features which prevent the canister and device from exhibiting a mutual "wobble" when connected together. Ribs (not shown) extending between the canister top closure member 288 and the inner face 300 of the upstanding flange 260 locate in grooves 302 in the device sidewalls when canister and device are connected. The casing 230 also houses all of the electrical equipment and control and power management features, the functioning of which was described briefly with respect to FIGS. 3 and 4 hereinabove. The side piece 238 is provided with a socket member 298 to receive a charging jack from an external mains powered battery charger (both not shown).

Figure 10A:
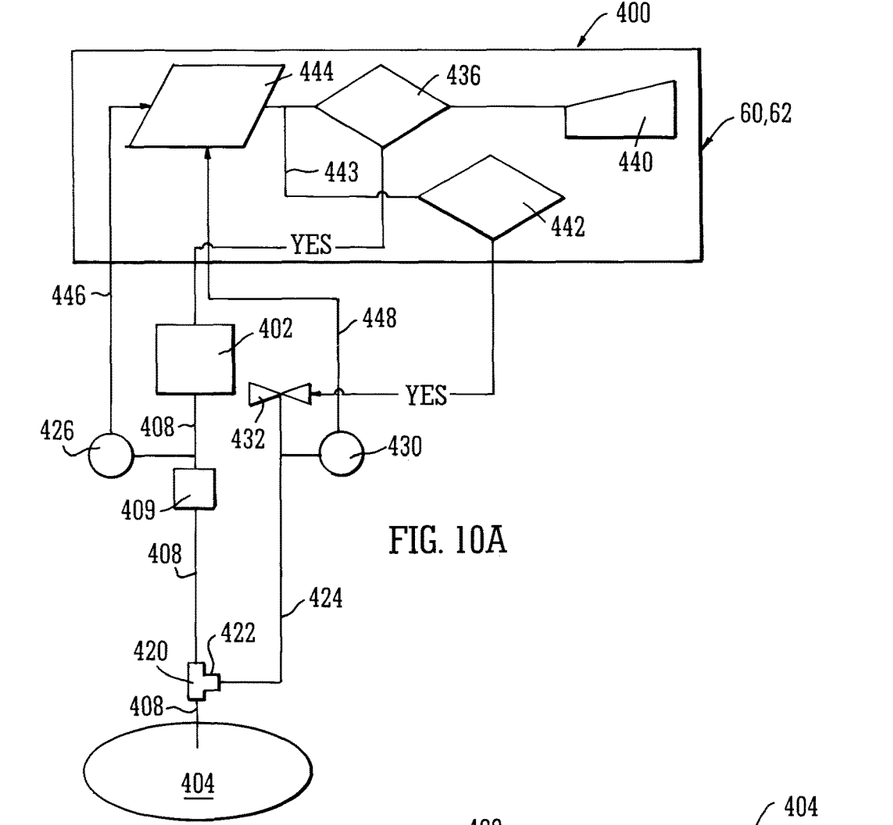
FIGS. 10A and 10B show a schematic drawing of a first embodiment of the present invention and part of a control system related to the operation of vacuum pump means and a control valve and, a schematic cross section of a wound site, respectively.

FIG. 10A shows a schematic representation of an apparatus 400 according to a first embodiment of the present invention. The apparatus comprises a vacuum pump 402 connected to a wound site 404 by an aspirant conduit 408 via a waste canister 409. As shown schematically in FIG. 10B the wound site 404 itself comprises a wound per se 406 having one end of the aspirant conduit 408 applied thereto and sealed into a wound cavity 410 formed by and overlying sealing drape film 412 which is sealed around the edges of the wound 406 by an adhesive layer (not shown) on the film 410 well known in the dressings art, to sound skin 414. The aspirant conduit 408 is sealed to the drape 412 at the point 416 at which it passes therethrough by, for example, pinching the self adhesive drape film around the conduit. The wound may or may not have a filler 418 of some kind therein as is known in the TNP therapy art. The conduit 408 is divided into two portions by a "T" piece 420 inserted close to the dressing drape 412 (see FIG. 10B) and having the branch portion 422 connected to a pressure sensing conduit 424. Aspirant conduit 408 is provided with a first pressure sensor 426 and conduit 424 is provided with a second pressure sensor 430. Pressure sensing conduit 424 is further provided with a valve 432 which may be an electrically operated solenoid valve, for example, and connected to a logic system 434 which is part of the control system 60 and user interface 62 (see FIGS. 1 to 4 and accompanying description). When the valve 432 is closed the conduit 424 is also closed constituting a blind branch of the aspirant conduit 408; and, when the valve 432 is open the conduit 424 is effectively open to the atmosphere. The valve 432 is provided with a microbial filter (not shown) to prevent bacteria from contaminating the device and/or being expelled to atmosphere. The pump 402 is connected to logic 436 in the control system to run the pump in response to settings provided by the user or a clinician by a user operated device 440 such as a keypad (not shown) to set a desired pressure, for example. Logic 442 in software is also provided to control the operation of the valve 432 in response to signals 443 in relation to pressure data from a diagnostic portion 444 of the control system 60 which signals are themselves provided in response to pressure data signals 446, 448 from the pressure sensors 426, 430, respectively.

Figures 10B, 11A:
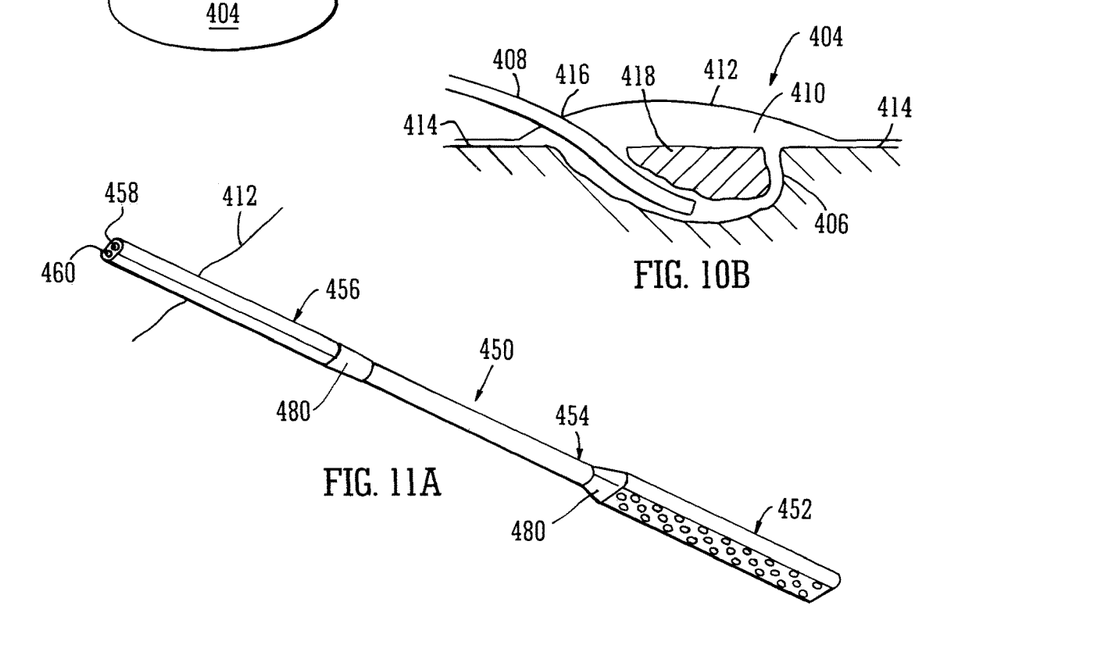
FIGS. 11A to 11D which show various views and cross sections of a purpose made drain/aspirant conduit for incorporation with a wound dressing and for use with apparatus according to the present invention; and, FIGS. 12A to 12C which show an embodiment of a flow splitting device for installation in an aspirant conduit.

In operation a user or clinician sets a pressure which it is desired to achieve at the wound cavity 410 by use of the user interface device 440 at which point the pump 402 is started by the logic software 436. The pump applies a vacuum to the wound cavity 410 via the aspirant conduit 408. Initially the pressures sensed by the sensors 426, 430 will be approximately equal. However, as aspiration of the wound cavity proceeds and wound exudate is drawn up the conduit 408 there will be growing pressure differential between the pressure sensed by the sensor 426 adjacent the pump 402 and that sensed by the sensor 430 adjacent the dressing/ wound site 404. This is normal as there must be a pressure differential between the pump 402 and the dressing/wound site 404 for exudate fluid to travel up the conduit 408 into the waste canister 409.

However, when the pressure differential between sensors 426, 430 reaches or exceeds a level stored in the memory of the diagnostic portion 444 of control system 60, the valve 432 is opened to atmosphere or ambient pressure by logic software 442. As discussed hereinabove, if the response of the pressure sensor 426 is to remain at the user-set pumping pressure and that pressure sensed by pressure sensor 430 is to fall (or rise) to ambient atmospheric pressure and for both to stay at these pressures for a predetermined time set in the control system memory, the control system will issue an alarm relating the need to check that the aspirant conduit is not physically constricted in some way or that the waste canister may be full and needs changing or replacing. Alternatively, on opening the valve 432, should the pressure indicated by sensor 430 fall (or rise) to ambient atmospheric pressure and, after a predetermined time interval set in the control system memory, the pressure indicated by sensor 426 also reach approximate parity with that indicated by 430, the valve 432 will close and the vacuum pump continue to aspirate the wound site 404. In this latter case the aspirant conduit is likely to have been blocked by exudate fluid and merely needing clearing with the aid of an air bleed provided by the pressure sensing conduit 424 being open to atmosphere.

Figure 11B:
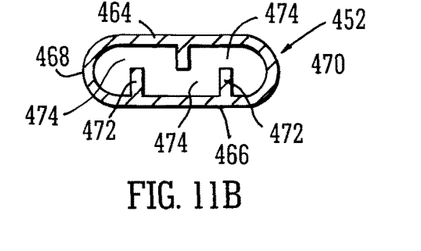
Figure 11C:
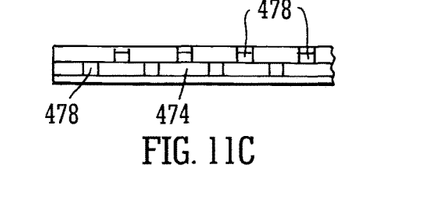
Figure 11D:
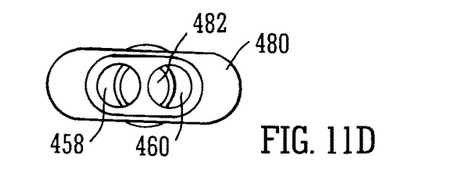

Referring now to FIGS. 11A to 11D which show a purpose made drain/aspirant conduit 450 for use in place of the plain conduit 408 shown in FIG. 10. FIG. 11A shows a perspective view of a complete drain/aspirant conduit; FIG. 11B shows a cross section through an exudate fluid collecting part. FIG. 11C shows a longitudinal cross-section through the exudate fluid collecting portion; and FIG. 11D shows a cross sectional view at a junction of single and dual-lumen portions of the conduit. The drain/aspirant conduit 450 is flexible and comprises a drain portion 452 for collecting exudate fluids from the wound cavity 410 (see FIG. 10B); a plain portion 454, preferably of length less than 300 mm and more preferably of length less than 100 mm, having a single lumen therethrough; and, a connection portion 456 comprising an aspirant conduit portion having two lumens 458, 460 therethrough and which part 456 lies outside of the dressing drape 412 so as to be able to be handled and manipulated by a clinician, for example. The drain portion 452 comprises a flattened outer shape having two opposing walls 464, 466 joined by curved wall portions 468, 470. The wall portions 464, 466 have on their inner surface longitudinally extending ribs 472 which prevent the soft, flexible material walls from being closed together against each other by the effects of atmospheric pressure existing outside of the dressing in which the drain/aspirant conduit is installed as in FIG. 10B. The ribs maintain longitudinal passages 474 even when the ends of the ribs 472 touch the inner surface of the opposing walls. The walls 468, 470 are provided with a plurality of holes 478 which permit exudate fluid to be sucked into and flow along the passages 474 towards the centrally positioned plain conduit portion 454. Wound exudate fluid flows along the conduit portion 454 to the dual-lumen portion 456 which joins the single lumen portion 454 at a junction portion 480 where the single lumen 482 of the portion 454 is divided. The end portion 462 of the dual-lumen conduit 456 may then be connected to an aspirant conduit to the vacuum pump device by, say lumen 458, and lumen 460 may be connected to a pressure sensing conduit having a pressure sensor and valve as in FIG. 10A, for example, thus bringing the aspirant conduit and pressure sensing conduit in fluid communication by the lumens 458 and 460.

Figure 12A:
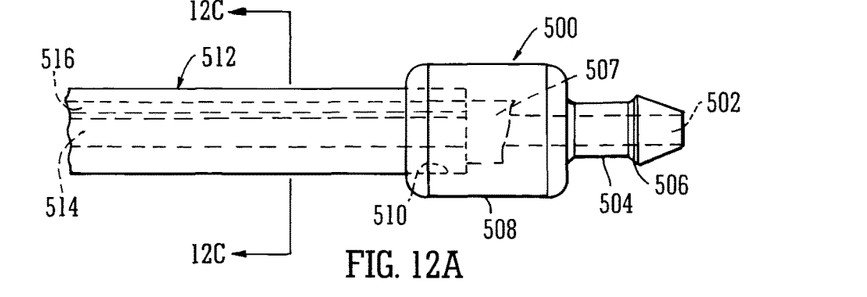
Figure 12B:
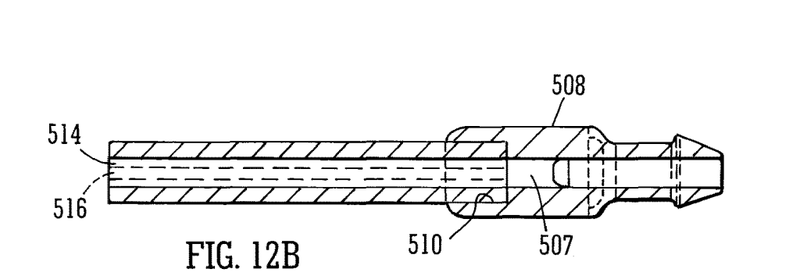
Figure 12C:
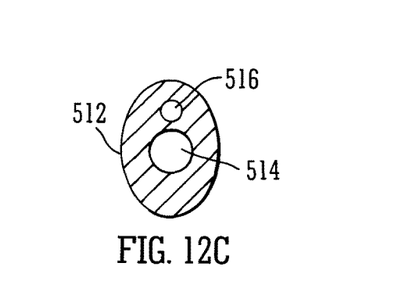

Referring now to FIG. 12 where FIG. 12A shows an axial cross section through a flow splitting connector device 500 and a portion of dual-lumen conduit 512 attached thereto; FIG. 12B shows a similar cross section but at 90° to that of FIG. 12A; and, FIG. 12C which shows a cross section through the dual lumen conduit 512 at 12C-12C of FIG. 12A. In effect the flow splitting connector 500 may replace the "T" piece 422 of FIG. 10A. The connector 500 comprises an inlet conduit portion 502 having a spigot 504 and shoulder 506 to prevent unwanted detachment from a single lumen drain conduit exiting a wound dressing as at 416 of FIG. 10B. The inlet conduit portion 502 becomes enlarged 507 within a body portion 508 and terminates at a socket portion 510 dimensioned and shaped to receive a dual lumen conduit 512. The dual lumen conduit 512 has two conduits: a large conduit 514 which forms the aspirant conduit to which a vacuum source (not shown) is attached and through which a (wound cavity) is aspirated to remove exudate to a waste receptacle (not shown); and, a smaller lumen 516 which may be connected to a second pressure sensor (not shown). In essence the lumen 514 is the aspirant conduit and corresponds to lumen 408 in FIG. 10A; the lumen 516 is the pressure sensing conduit and corresponds to lumen 424 in FIG. 10A; and, the region 507 where the inlet conduit becomes enlarged is the point where the aspirant conduit 514 and the pressure sensing conduit 516 are in fluid communication with each other and corresponds to the "T"-piece 420 of FIG. 10A.

Throughout the description and claims of this specification, the words "comprise" and "contain" and variations of the words, for example "comprising" and "comprises", means "including but not limited to", and is not intended to (and does not) exclude other moieties, additives, components, integers or steps.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith.

What is claimed is:

1. A negative pressure wound therapy apparatus comprising:
    a dual lumen conduit comprising first and second lumens;
    a negative pressure source configured to provide negative pressure to a wound covered by a wound dressing via a fluid flow path comprising the first lumen of the dual lumen conduit and to aspirate fluid from the wound via the fluid flow path;
    a pressure sensor configured to sense pressure in the second lumen of the dual lumen conduit;
    a valve configured to selectively provide fluid communication between the second lumen of the dual lumen conduit and atmosphere; and
    a controller configured to detect and/or clear a blockage in the fluid flow path, the controller further configured to:
        determine a pressure difference between a pressure level provided by the negative pressure source and a pressure level in the second lumen of the dual lumen conduit sensed by the pressure sensor, in response to a determination that the pressure difference satisfies a blockage threshold, open the valve to introduce atmospheric air to attempt to clear the blockage in the fluid flow path.

2. The apparatus of claim 1, wherein the controller is further configured to indicate blockage in the fluid flow path in response to a determination that the pressure difference is not substantially zero after a time interval has expired.

3. The apparatus of claim 2, wherein the controller is further configured to close the valve in response to a determination that the pressure difference has substantially reached zero prior to expiration of the time interval.

4. The apparatus of claim 1, wherein the controller is further configured to indicate a leak in the fluid flow path in response to a determination that the pressure difference satisfies a leakage threshold.

5. The apparatus of claim 4, wherein the leakage threshold is substantially zero.

6. The apparatus of claim 4, wherein the controller is further configured not to open the valve in response to the determination that the pressure difference satisfies the leakage threshold.

7. The apparatus of claim 1, further comprising an additional pressure sensor configured to sense pressure in the fluid flow path, wherein the pressure difference comprises a difference between pressure levels sensed by the pressure sensor and the additional pressure sensor, and wherein the controller is further configured to indicate blockage in the fluid flow path in response to a determination that the pressure difference is not substantially zero after a time interval has expired.

8. The apparatus of claim 7, wherein the controller is further configured to close the valve in response to a determination that the pressure difference has substantially reached zero prior to expiration of the time interval.

9. The apparatus of claim 7, wherein the controller is further configured to indicate a leak in the fluid flow path in response to a determination that the pressure difference satisfies a leakage threshold, wherein the leakage threshold is substantially zero.

10. The apparatus of claim 9, wherein the controller is further configured not to open the valve in response to the determination that the pressure difference satisfies the leakage threshold.

11. The apparatus of claim 1, further comprising a filter covering the valve, the filter configured to substantially prevent release of bacteria into the atmosphere.

12. The apparatus of claim 1, wherein the fluid flow path further comprises a canister configured to store at least a portion of fluid aspirated from the wound.

13. A method of controlling a negative pressure wound therapy apparatus, the method comprising:
by a negative pressure source configured to be fluidically connected to a wound covered by a wound dressing, providing negative pressure to the wound via a fluid flow path comprising a first lumen of a dual lumen conduit;
by a pressure sensor, sensing pressure in a second lumen of the dual lumen conduit;
by a controller, detecting and/or clearing a blockage in the fluid flow path by:
determining a pressure difference between the provided negative pressure level and the sensed pressure in the second lumen of the dual lumen conduit,
in response to a determining that the pressure difference satisfies a blockage threshold, opening a valve to introduce atmospheric air into the fluid flow path in order to attempt to clear the blockage in the fluid flow path.

14. The method of claim 13, further comprising, by the controller, indicating blockage in the fluid flow path in response to determining that the pressure difference is not substantially zero upon expiration of a time interval.

15. The method of claim 14, further comprising, by the controller, stopping the introduction of atmospheric air into the fluid flow path in response to determining that the pressure difference has substantially reached zero prior to expiration of the time interval.

16. The method of claim 13, further comprising, by the controller, indicating a leak in the fluid flow path in response to determining that the pressure difference satisfies a leakage threshold, wherein the leakage threshold is substantially zero.

17. The method of claim 16, further comprising, by the controller, not introducing atmospheric air into the fluid flow path in response to determining that the pressure difference satisfies the leakage threshold.

18. The method of claim 13, further comprising, by an additional pressure sensor, sensing pressure in the fluid flow path, wherein the pressure difference comprises a difference between pressure levels in the fluid flow path and the second lumen, and, by the controller, indicating blockage in the fluid flow path in response to determining that the pressure difference is not substantially zero upon expiration of a time interval.

19. The method of claim 18, further comprising, by the controller, stopping the introduction of atmospheric air into the fluid flow path in response to determining that the pressure difference has substantially reached zero prior to expiration of the time interval.

20. The method of claim 18, further comprising, by the controller, indicating a leak in the fluid flow path in response to determining that the pressure difference satisfies a leakage threshold, wherein the leakage threshold is substantially zero.

21. The method of claim 20, further comprising, by the controller, not introducing atmospheric air into the fluid flow path in response to determining that the pressure difference satisfies the leakage threshold.

22. A negative pressure wound therapy apparatus comprising:
a dual lumen conduit comprising first and second lumens;
a negative pressure source configured to provide negative pressure to a wound covered by a wound dressing via a fluid flow path comprising the first lumen of the dual lumen conduit and to aspirate fluid from the wound via the fluid flow path;
a pressure sensor configured to sense pressure in the fluid flow path;
a valve configured to selectively provide fluid communication between the second lumen of the dual lumen conduit and atmosphere; and
a controller configured to detect and/or clear a blockage in the fluid flow path, the controller further configured to:
open the valve to introduce atmospheric air into the fluid flow path,
determine if pressure in the fluid flow path sensed by the pressure sensor decreases by at least a threshold amount over a duration of time, and
in response to determining that the pressure in the fluid flow path has not decreased by the at least the threshold amount over the duration of time, indicate presence of blockage in the fluid flow path.

23. The apparatus of claim 22, wherein the controller is further configured to:
in response to determining that the pressure in the fluid flow path has decreased by the at least the threshold amount, close the valve.

24. The apparatus of claim 22, further comprising a filter covering the valve, the filter configured to substantially prevent release of bacteria into the atmosphere.

25. The apparatus of claim 22, wherein the fluid flow path further comprises a canister configured to store at least a portion of fluid aspirated from the wound.

26. The apparatus of claim 22, wherein the negative pressure source comprises a pump.

27. A method of controlling a negative pressure wound therapy apparatus, the method comprising:
by a negative pressure source, providing negative pressure to a wound covered by a wound dressing via a fluid flow path comprising a first lumen of a dual lumen conduit and aspirating fluid from the wound via the fluid flow path; and
by a controller, detecting and/or clearing a blockage in the fluid flow path by:
opening a valve configured to selectively provide fluid communication between a second lumen of the dual lumen conduit and atmosphere to introduce atmospheric air into the fluid flow path,
determining if pressure in the fluid flow path sensed by a pressure sensor decreases by at least a threshold amount over a duration of time, and
in response to determining that the pressure in the fluid flow path has not decreased by the at least the threshold amount over the duration of time, indicating presence of blockage in the fluid flow path.

28. The method of claim 27, further comprising, by the controller:
in response to determining that the pressure in the fluid flow path has decreased by the at least the threshold amount, closing the valve.

29. The apparatus of claim 27, further comprising storing at least a portion of fluid aspirated from the wound in a canister.

* * * * *

UNITED STATES PATENT AND TRADEMARK OFFICE
CERTIFICATE OF CORRECTION

| | |
|---|---|
| PATENT NO. | : 10,646,624 B2 |
| APPLICATION NO. | : 15/479837 |
| DATED | : May 12, 2020 |
| INVENTOR(S) | : Edward Yerbury Hartwell |

It is certified that error appears in the above-identified patent and that said Letters Patent is hereby corrected as shown below:

In the Specification

In Column 11, Line 39, delete "Theses" and insert --These--.

In Column 11, Line 44, delete ""0"" and insert --"O"--.

In Column 12, Line 28, delete "self adhesive" and insert --self-adhesive--.

In the Claims

In Column 18, Line 18, Claim 29 delete "apparatus" and insert --method--.

Signed and Sealed this
Third Day of September, 2024

Katherine Kelly Vidal
*Director of the United States Patent and Trademark Office*